United States Patent
Tovey et al.

(10) Patent No.: US 10,271,539 B2
(45) Date of Patent: Apr. 30, 2019

(54) ASSAY-READY FROZEN CELL AND METHOD FOR MINIMIZING VARIABILITY IN THE PERFORMANCE THEREOF

(71) Applicants: LE CENTRE NATIONALE DE LA RECHERCHE SCIENTIFIQUE (CNRS), Paris (FR); BIOMONITOR LIMITED, Galway (IE)

(72) Inventors: Michael G. Tovey, Paris (FR); Christophe Lallemand, Paris (FR)

(73) Assignees: LE CENTRE NATIONALE DE LA RECHERCHE SCIENTIFIQUE (CNRS), Paris (FR); BIOMONITOR LIMITED, Nuig Galway (IE)

( * ) Notice: Subject to any disclaimer, the term of this patent is extended or adjusted under 35 U.S.C. 154(b) by 0 days.

(21) Appl. No.: 15/038,680

(22) PCT Filed: Nov. 21, 2014

(86) PCT No.: PCT/US2014/066746
§ 371 (c)(1),
(2) Date: May 23, 2016

(87) PCT Pub. No.: WO2015/077523
PCT Pub. Date: May 28, 2015

(65) Prior Publication Data
US 2016/0302405 A1     Oct. 20, 2016

Related U.S. Application Data

(60) Provisional application No. 61/907,631, filed on Nov. 22, 2013, provisional application No. 61/920,061, filed on Dec. 23, 2013.

(51) Int. Cl.
*A01N 1/02*     (2006.01)
(52) U.S. Cl.
CPC ......... *A01N 1/0221* (2013.01); *A01N 1/0226* (2013.01)
(58) Field of Classification Search
None
See application file for complete search history.

(56) References Cited

U.S. PATENT DOCUMENTS

| | | |
|---|---|---|
| 4,052,817 A | 10/1977 | Seibert |
| 2003/0049840 A1 | 3/2003 | Demetriou et al. |
| 2008/0026361 A1* | 1/2008 | Ostermeier ............. A01N 1/02 435/2 |

FOREIGN PATENT DOCUMENTS

| | | | |
|---|---|---|---|
| EP | 2045306 A1 | 4/2009 | |
| JP | 2006/507817 A | 3/2006 | |
| JP | 2010/273549 A | 12/2010 | |
| WO | 9203046 A1 | 3/1992 | |
| WO | WO 9203046 A1 * | 3/1992 | ............. A01N 1/02 |
| WO | 9935255 A2 | 7/1999 | |
| WO | 2004039990 A2 | 5/2004 | |
| WO | 2012/164321 A1 | 12/2012 | |

OTHER PUBLICATIONS

"Murashige and Skoog Basal Medium", Feb. 1, 2010 (Feb. 1, 2010), pp. 1-1, XP055168663, St. Louis, MO, U.S. A., Retrieved from the Internet: https://www.sigmaaldrich.com/content/dam/sigma-aldrich/docs/Siga/Product_Information_Sheet/1/m5519pis.pdf (retrieved on Feb. 10, 2010).

Weetall M et al: "A Homogeneous Fluorometric Assay for Measuring Cell Adhesion to Immobilized Ligand Using V-Well Microtiter Plates", Analytical Biochemistry, vol. 293(2):277-287 (2001).

"RPMI-1640 Productinformation", Internet Citation, May 29, 2003, Retrieved from the Internet: http://www.sigmaaldrich.com/sigma/datasheet/r6504dat.pdf (retrieved on Oct. 26, 2005).

Kunapuli et al., Application of Division Arrest Technology to Cell-Based HTS: Comparison With Frozen and Fresh Assay and Drug Development Technologies, 3(1):17-26, (2005).

* cited by examiner

*Primary Examiner* — Emily A Cordas
(74) *Attorney, Agent, or Firm* — Browdy and Neimark, PLLC

(57) ABSTRACT

The invention provides an assay-ready frozen eukaryotic cell (stored frozen) in a composition that includes a cryopreservative and an inhibitor of xanthine oxidase, a kit containing a plurality of the assay-ready frozen eukaryotic cell, and a method of preparation thereof to minimize the variability in the performance of the cell, particularly in terms of undesirable intra- and inter-assay variability.

29 Claims, 6 Drawing Sheets

ASSAY-READY FROZEN CELL AND METHOD FOR MINIMIZING VARIABILITY IN THE PERFORMANCE THEREOF

BACKGROUND OF THE INVENTION

Field of the Invention

The present invention relates to the field of assay-ready frozen cells.

Description of the Related Art

The use of assay ready frozen cells allows cell-based assays to be carried out without the need for cell culture or the maintenance of cells continuously in the laboratory, thereby greatly reducing costs and increasing the applicability of cell-based assays to routine use in screening assays and diagnostics. Assay-ready frozen cells often exhibit a markedly reduced sensitivity, however, relative to that of continuously cultured cells when used in a particular assay. In addition, individual lots of cells as well as individual vials of assay-ready frozen cells often exhibit a high degree of both intra- and inter-assay variability in their performance. Treatment of cells with vinblastin provides a means of preventing cell proliferation without reducing assay sensitivity thereby allowing the commercialization of assay-ready frozen cells while preventing a customer from cultivating the cells themselves (WO2004/039990; US2004/0235157; U.S. Pat. No. 7,470,536).

Treatment of cells with vinblastin and subsequent freezing can lead to apoptosis and cell lysis resulting from vinblastin treatment and the formation of ice crystals respectively. This results in the activation and release of various proteases (caspases, cathepsons, and calpains) into the cytosol. Apoptosis and/or cell lysis can also lead to ubiquitination and hence increased proteasomal activity. Reactive oxygen species (ROS) are also released and can create a state of oxidative stress. All of the above can potentially alter or impair bioluminescent enzyme activity and interfere with the outcome of reporter-gene assays. Firefly luciferase (FL) is generally less stable than Renilla luciferase (RL) and more sensitive to inactivation in apoptotic cells. In addition, reactive oxygen species can also activate and modulate certain signal transduction pathways such as the NFkB pathway leading for example to variability in TNFα induced FL readings. One approach to overcome such problems is to engineer the bioluminescent proteins to increase their stability for example by mutating a protease cleavage site; or increasing pH stability or thermo-stability (Law et al., 2006; Baggett et al., 2004; Thompson et al., 1997; Loening et al., 2006). An alternative approach that is more rapid, inexpensive, and generally applicable to different types of assays is described herein as the subject of the present invention.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides an assay-ready frozen eukaryotic cell (stored frozen) in a composition that includes a cryopreservative and an inhibitor of xanthine oxidase and a method of preparation thereof to minimize the variability in the performance of the cell, particularly in terms of undesirable intra- and inter-assay variability.

The present invention also provides a kit containing a plurality of the assay-ready frozen eukaryotic cell of the present invention.

DETAILED DESCRIPTION OF THE INVENTION

Figure 1A:
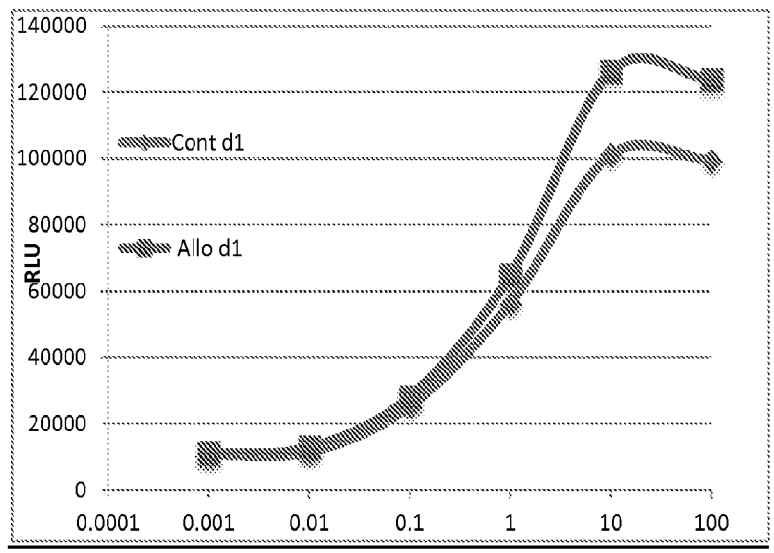
FIGS. 1A and 1B are graphs showing the relative luciferase units (RLU) for KJL-2 cells after freezing for one day (FIG. 1A) or 5 days (FIG. 1B) in the preferred cryopreservative solution disclosed in WO2004/039990; US 2004/0235157 and U.S. Pat. No. 7,470,536 (i.e., 40% fetal bovine serum (FBS) and 2.5% dimethylsulfoxide+10% glycerol) with or without (control) the presence of 100 μM allopurinol, where the FL and RL reporter gene products induced by TNFα were assayed (after thawing the frozen cells) using the Promega DUAL-GLO system (a luciferase substrate that allows the sequential quantification of firefly luciferase (FL) and Renilla luciferase (RL) activity each to be determined over a period of several minutes in the same well of a microtiter plate). The X-axis is TNFα, ng/ml.

The present invention provides an assay-ready eukaryotic cell that is stored frozen in such a manner as to minimize the variation (intra- and inter-assay variability between individual lots and between individual containers, e.g., vials or multiwall plates, or kits) in the performance of assay-ready frozen cells, upon thawing, for a desired assay. Such an assay ready frozen cell which has the advantageous property of minimized (i.e., low, insignificant or negligible) intra- and inter-assay variability in performance between individual lots or containers is of commercial importance as an unmet need. A suitable eukaryotic cell that is to be used in a desired assay, such as a reporter-gene assay, can be prepared to be an assay-ready frozen cell according to the present invention by preparing the eukaryotic cell for frozen storage by bringing the cell into contact with a composition that contains a cryopreservative and an inhibitor of xanthine oxidase. Accordingly, the assay-ready eukaryotic cell of the present invention is part of a composition which contains an inhibitor of xanthine oxidance and a cryopreservative, and is stored frozen in this composition.

The eukaryotic cell that is made an assay-ready frozen eukaryotic cell according to the present invention can include any of the many eukaryotic cells commonly used in assays, such as, e.g., enzyme assays and reporter-gene assays. Non-limiting examples include a mammalian, avian (preferably chicken), fish (preferably zebrafish), insect, and yeast cell. The mammalian cell is preferably a human cell and more preferably a human promonocytic cell (most preferably a PIL5 cell carrying the ISRE-luc vector containing the firefly luciferase gene reporter construct and disclosed in U.S. Pat. No. 7,470,536) or a human erythroleukemia cell (most preferably a KJL-2 cell, derived from the K562 cell line under ATCC Accession no. CCL-243, a chronic myelogenous leukemia). Other preferred cell lines include, but are not limited to, human myeloid (i.e., U266R), human T-cell lymphoma (i.e., Jurkatt), human breast adenocarcinoma (i.e., MCF7) cell lines and mouse lymphoma (i.e., L1210) and mouse erythroid leukemia cell lines.

The inhibitor of the xanthine oxidase enzyme in the composition in which the eukaryotic cell is present for the process of freezing (and storing frozen) serves to inhibit hydrogen peroxide production (and perhaps also acts in other as yet undetermined manner). Non-limiting examples of an inhibitor of xanthine oxidase include allopurinol, oxypurinol, tisopurine, febuxostat, and inositols (such as phytic acid and myo-inositol). The preferred inhibitor of xanthine oxidase is allopurinol, and the allopurinol concentration in the composition in which the eukaryotic cell is stored is in a range of about 50 to 200 µM, more preferably about 75 to 150 µM, and most preferably 100 µM. Mixtures of inhibitors of xanthine oxidase are also contemplated in the composition for storing the cell.

In one preferred embodiment of the present invention, the composition also includes a scavenger of reactive oxygen species (ROS). Many scavengers of ROS (e.g., hydrogen peroxide) are known in the art, but N-acetylcystine (NAC) and glutathione SH (GSH) are preferred. When NAC is used as the scavenger of ROS in the composition, the concentration of NAC is in a range of about 1 mM to 10 mM, preferably in a range of 2.5 mM to 5 mM, and more preferably is 5 mM. When GSH is used in the composition, the concentration of GSH is in a range of about 0.5 mM to 5 mM, preferably in a range of about 1 mm to 2 mM, and more preferably is 1 mM. Mixtures of scavengers can be used including mixtures of NAC and GSH.

The assay-ready eukaryotic cell according to the present invention is preferably a cell (e.g., after having been transformed/transfected with a DNA construct such as a reporter gene construct for the detection in an assay of a molecule or signal of interest) which has been treated with an anti-mitotic or pro-apoptotic chemical agent such as vinblastin, cisplatin, doxorubicin, or an anti-tumor intercalating agent (i.e., mitomycin C) in a sufficient amount and for a sufficient time such that the treated cell maintains the signal transduction activity of the cell surface protein or pattern recognition receptor for a period of at least about 1 hour but no more than about 30 days at a temperature above freezing following treatment with the agent, after which period of time the treated cell immediately undergoes cellular death. Many reporter gene constructs are well known in the art. The DNA construct that may be carried by the cell is preferably one that contains a nucleotide sequence encoding a reporter gene product operatively linked to one or more transcriptional control elements that is regulated by the signal transduction activity of a cell surface protein in response to an extracellular signal. Non-limiting preferred examples of the DNA construct as well as the cell for assay are disclosed in WO2004/039990; US2004/0235157; U.S. Pat. No. 7,470,536; WO2008/055153; US20080138818; WO2009/058884; US20090136947; U.S. Pat. No. 8,426,123; WO2009/111572; and US20110189658, which are incorporated herein by reference.

An anti-mitotic or pro-apoptotic agent will affect a treated cell when it begins to replicate, such as for example by preventing spindle formation, thereby inducing apoptosis and killing the cell. Thus, cells which have been treated with an anti-mitotic or pro-apoptotic agent, such as transformed human promonocytic cells, will have a shelf life of about 24 hours during which the signal transduction assay can be conducted and after which period of time the cells will die. It will be appreciated that a cell having only a 24 hour shelf life is not desirable from a commercial standpoint. In order to extend the shelf life and minimize the intra- and inter-assay variability in performance of the cells, the treated cells are immediately washed to remove residual anti-mitotic or pro-apoptotic agent (i.e., remove the treated eukaryotic cell from further contact with the anti-mitotic or pro-apoptotic agent), and then brought into contact (such as by resuspension of the cell or plurality of cells) with the composition that includes a cryopreservative and an inhibitor of xanthine oxidase according to the present invention as disclosed above. Once the cell(s) are brought into contact with cryopreservation composition, they are immediately frozen, in which state they will have a much longer shelf life, depending upon the manner of freezing and thawing. Once thawed, however, cells that have been treated with an anti-mitotic or pro-apoptotic agent must be used within 24 hours, after which they will undergo cellular death (i.e., apoptosis). It should recognized here that, while the assay-ready eukaryotic cell of the present invention is preferably one which has been treated with an anti-mitotic or pro-apoptotic agent such as disclosed in WO2004/039990; US2004/0235157; U.S. Pat. No. 7,470,536; WO2009/058884; US20090136947; U.S. Pat. No. 8,426,123; WO2009/111572; and US20110189658, which are incorporated herein by reference, the assay-ready eukaryotic cell of the present invention is not limited to such a treated cell. A cell not treated with an anti-mitotic or pro-apoptotic agent for use in an assay at a later time can be prepared to be assay-ready and frozen in the same manner as discussed herein except that it is untreated with an anti-mitotic or pro-apoptotic agent.

Conventional wisdom is that cryopreservation of cells requires a special freezing and thawing process (and equipment) in which the cells are frozen at a rate of about 1° C. per minute until it reaches −80° C. or liquid nitrogen temperatures of about −200° C., where it may be stored indefinitely, and after which it must be thawed very rapidly. A storage temperature of at or about −80° C. is preferred. Often, dimethyl sulfoxide (DMSO) or another cryopreservative is also used in order to help protect the cells. While glycerol is also a known cryopreservative compound that will protect cells, there is the possibility that it may prevent protein ligands from interacting with surface receptors at the high percentage (50%) of glycerol conventionally used for cryopresevation. However, a low percentage of glycerol (much less than the 50% conventionally used) can be used. DMSO does not have this disadvantage. After treating with an anti-mitotic or pro-apoptotic agent, a cell may achieve a long shelf life if, prior to freezing, it is brought into contact with a composition that includes an inhibitor of xanthine oxidase and a cryopreservative such as DMSO so that once thawed such a cell will remain active, i.e., for signal transduction assays used for determining the amount of ligand or neutralizing antibodies to the ligand or to an anti-ligand antibody, for approximately 24 hours until it undergoes apoptosis as a result of being treated with an anti-mitotic and pro-apoptotic agent. Any anti-mitotic or pro-apoptotic agent which kills cells during the process of replication by inducing apoptosis, such as γ-radiation and chemical agents such as vinbastin, 5-FU, cisplatin, doxorubicin, or an anti-tumor intercalating agent (i.e., mitomycin C) can be used for this purpose as it would be expected that the cells will remain biologically active during a quiescent period and until such time the treated cells start to die.

The treated transformed cell (e.g., transformed with a DNA construct, such as with a reporter gene construct) is frozen at a temperature and under conditions such that it will resume signal transduction after thawing. While the cell is preferably frozen at a temperature at or about −80° C., it is intended that other suitable temperatures for cryopreservation of cells, such as the liquid nitrogen temperature of about −200° C., be encompassed as well. This applies to all cells, whether treated or untreated with an anti-mitotic or pro-apoptotic agent. The cell is brought into contact (e.g., resuspended) with a composition that includes an inhibitor of xanthine oxidase and a cryopreservative before freezing the cell. Dimethyl sulfoxide (DMSO) is the preferred cryopreservative although other suitable cryopreservatives which have a high bonding affinity to water, such as ethylene glycol, polyethylene glycol, propylene glycol, glycerol, butane diol, propanediol, and formamide, may be used so long as they are suitable at the final temperature for freezing and do not interfere with the use of the cell after thawing. When DMSO is used alone as the cryopreservative, the solution containing DMSO preferably contains about 10% DMSO. More preferably, 2.5% DMSO is used in combination with 10% glycerol as the cryopreservative. The presence of fetal bovine serum (FBS) is also preferred in the composition, particularly in the amount of about 40% FBS.

A further aspect of the present invention is a method for preparing the assay-ready frozen eukaryotic cell and involves adding a composition that includes a cryopreservative and an inhibitor of xanthine oxidase to a eukaryotic cell (treated or untreated with an anti-mitotic or pro-apoptotic agent), and cooling the cell at a rate of preferably about 1° C. per minute until about −80° C. for frozen storage of the assay-ready eukaryotic cell to thereby improve the performance, upon thawing, of the assay-ready cell in an assay. While the rate of about 1° C. per minute is most preferred, partly because the equipment for doing so is commonly used in the art, a slightly modified rate of freezing which can be empirically determined by routine experimentation, such as between about 0.5° C. and 1.5° C. may be suitable as well. A plurality of assay-ready frozen eukaryotic cells prepared in such a manner can be stored frozen in a plurality of separate individual vials or containers with the method advantageously minimizing the variability between individual vials or containers (e.g., in intra- and inter-assay variability) in the performance of the assay-ready frozen eukaryotic cells, upon thawing, in an assay.

The cell, when treated with an anti-mitotic or pro-apoptotic agent, results in a commercial cell line that has the commercially desirable properties of a sufficient shelf life for the purpose of the assay and of being a one time use cell that cannot be propagated for possible further use. Preferably, the cell is treated either 1) by irradiating with 6 to 12 Gy of γ radiation, more preferably about 9 Gy, and storage at room temperature for up to 14 days after irradiation or 2) by exposure to an anti-mitotic or pro-apoptotic agent, such as vinblastin, cisplatin, or 5-fluorouracil, most preferably vinblastin, for 10 minutes at 37° C., both prior to resuspending in most preferably a solution/composition containing 40% fetal bovine serum (FBS) and 2.5% DMSO+10% glycerol, 100 μM allopurinol+(5 mM NAC or 1 mM GSH) and freezing at −80° C. A cell untreated with an anti-mitotic or pro-apoptotic agent may be brought into contact with most preferably a solution/composition containing 2.5% DMSO+10% glycerol, 100 μM allopurinol+(5 mM NAC or 1 mM GSH), optionally 40% or a lower amount of FBS, and freezing at −80° C.

Those of ordinary skill in the art, based on the guidance provided herein, would recognize that the parameters (some of which would not be applicable when the cell is a cell not treated with an anti-mitotic or pro-apoptotic agent) which can be varied to further optimize the composition and conditions include:

1) Concentration of FBS. Besides FBS, most any serum could be used as it acts as a toxic sink to protect the cells from toxins, such as while being thawed or while being treated with an anti-mitotic or pro-apoptotic agent. The concentration of FBS can cause the results to vary.

2) Time is a variable. The amount of time of exposure to an anti-mitotic or pro-apoptotic chemical agent, such as vinblastin, before the cells are centrifuged out and washed to remove the agent (i.e., vinblastin).

3) Using vinblastin as a non-limiting example, the formulation of the vinblastin makes a difference. Presently, soluble vinblastin in a proprietary prebuffered formulation sold by Eli Lilly under the name Velbe in France is preferably used. A different formulation may require a slightly different combination of parameters.

4) The concentration of vinblastin.

5) Cell concentration during the vinblastin treatment.

6) The amount of cryopreservative or combination of cryopreservatives.

All of these parameters can be varied empirically and the results after freezing tested for sensitivity and precision and intra- and inter-assay variability after being thawed. This can be readily determined by one of ordinary skill in the art without undue experimentation, particularly in view of the guidance provided in the experiments shown herein and in FIGS. 11-24 for PIL5 cells in WO 2004/039990; US 2004/023517; and U.S. Pat. No. 7,470,536. The cells treated with an anti-mitotic or pro-apoptotic agent are those with substantially the same sensitivity as the untreated live cells for a period of at least one hour, preferably 8-24 hours, following thawing but having a viability of no more than 30 days, preferably no more than 14 days, more preferably no more than 5 days, most preferably no more than 3 days.

Exemplified below are protocols for preparation of microtiter assay plates and ampoules/vials of PIL5 cells (as model cells) treated with the anti-mitotic and pro-apoptotic agent 1 μg/ml vinblastin for 10 minutes at 37° C. prior to frozen storage at −80° C. and thawing at a later time for purposes of conducting the assay.

Preparation of Microtiter Assay Plates

1. PIL5 cells at a concentration of about $2 \times 10^5$ to $7 \times 10^5$ cells/ml in RMPI 1640 medium with 10% fetal bovine serum (FBS) are treated with a fresh solution of 1 μg/ml vinblastin (commercially available from Eli Lilly under the pre-buffered formulation VELBE), diluted from 1 mg/ml in $H_2O$, for 10 minutes at 37° C. in an atmosphere of 5% $CO_2$ in air. A $CO_2$ incubator can be used for convenience.

2. The PIL5 cells are centrifuged at 800×g for 10 minutes at 4° C., and washed once with the same volume of RPMI 1640 medium with 10% FBS to remove the vinblastin.

3. The PIL5 cells are re-suspended at a concentration of $2\times10^7$ cells/ml in RMPI 1640 medium with 40% fetal bovine serum (FBS), 2.5% dimethylsulfoxide+10% glycerol, and 100 μM allopurinol+(5 mM NAC or 1 mM GSH).

4. The cell suspension is dispensed into the wells of a flat-bottom micro-plate to give 300,000 cells per well (equivalent to 25 μl of cell suspension per well).

5. The micro-plate is frozen at −80° C. in an aluminum bag sealed under vacuum with the cover uppermost.

6. The micro-plates can be subsequently stored for limited periods at −20° C. until use.

Alternatively, PIL5 cells at a concentration of $2\times10^7$ cells/ml in RMPI 1640 medium with 40% fetal bovine serum (FBS) and 2.5% dimethylsulfoxide+10% glycerol can be frozen at −80° C. or −200° C. in a single or multiple cryopreservation vials. Immediately prior to use the vial is thawed rapidly and the cells distributed into one or more microtiter plates. Vials may also be prepared containing sufficient cells for half or a quarter of a microtiter plate as required.

It is preferred that the temperature at which the cells are frozen be about −80° C. and that the cells are resuspended in a solution, e.g., RPMI 1640 medium, with about 100 μM allopurinol, about 2.5 to 5 mM NAC (preferably about 5 mM), containing cryopreservatives, which are preferably about 2.5% DMSO+about 10% glycerol, prior to freezing. FBS in the amount of 40% or less may be advantageously included when appropriate.

A further aspect of the present invention is a kit containing a plurality of the assay-ready frozen eukaryotic cells. This kit for use in conducting an assay includes a testing device having a plurality of wells and a reagent containing a plurality of such an assay-ready frozen cell according to the present invention. Preferably, the testing device is a multi-well microtiter plate, but can also be any type of receptacle, such as petri dishes or plates, with a plurality of wells in which an assay can be conducted. It is preferred that the reagent containing a plurality of the assay-ready frozen eukaryotic cell is already disposed in the wells of the testing device, although it will be appreciated that such cells can instead be dispensed in the wells of the testing device by the end user just prior to conducting the assay. The kit may further include a set of instructions for using the kit to conduct the intended assay.

Having now generally described the invention, the same will be more readily understood through reference to the following example which is provided by way of illustration and is not intended to be limiting of the present invention.

EXAMPLE

Briefly, untreated cells or cells treated with vinblastin as described in WO 2004/039990; US 2004/0235157 and U.S. Pat. No. 7,470,536 were treated for 10 minutes with substances that inhibit the formation of reactive oxygen species and/or scavengers of reactive oxygen species either alone or concomitantly with vinblastin treatment. The cells were then frozen using the cryopreservative medium described in WO 2004/039990; US 2004/0235157 and U.S. Pat. No. 7,470,536 with or without substances that inhibit the formation of reactive oxygen species and/or scavengers of reactive oxygen species. KJL-2 cells were used in all experiments (carried out to date). All groups were treated with vinblastin using the same procedure as described in WO 2004/039990; US 2004/0235157 and U.S. Pat. No. 7,470,536. In order to reduce the formation of ice crystals and subsequent cell lysis, all experimental groups were frozen using the alcohol-free Biocison controlled freezing system that cools cells at approximately 1.0° C./minute. All assays were performed using DUAL-GLO (Promega, Catalogue No 2920) that allows Firefly luciferase (FL) and Renilla luciferase (RL) activity to be determined sequentially in the same well of a microtiter plate.

Results

Treatment of KJL-2 (derived from the K562 cell line under ATCC Accession no. CCL-243, a chronic myelogenous leukemia cells) with 10 micromolar staurosporine, a drug that induces apoptosis, inhibits FL activity progressively over 24 hours while RL activity remains fairly constant.

Pre-treatment of cells with various protease inhibitors (Pepstatin A, PMSF, ammonium chloride, etc), and addition of the protease inhibitors to the freezing medium did not significantly increase FL activity.

Pre-treatment of cells with the proteasome inhibitors MG-132, epoxomicin and lactacystin did not increase FL activity significantly. MG-132, that is known to inhibit NFkB signal transduction, reduced FL activity (Nakajima et al., 2011). Furthermore, certain signal transduction pathways such as the β-catenin pathway require a functional proteosome (Jüllig et al., 2006).

A number of free radicals are also produced during oxidative stress including superoxide $O_2^-$, hydroxyl radical (—OH) and hydrogen peroxide $H_2O_2$.

The cell permeable $O_2^-$ scavengers Tiron, and TEMPOL were both without effect on the FL/RL ratio.

MNTMPyP, a cell permeable superoxide dismutase (SOD) mimetic, was also without effect on the FL/RL ratio.

Mannitol, a specific —OH scavenger and the iron chelator deferoxamine, and the copper chelator tetra ethylenepentamine were also without effect on the FL/RL ratio.

Substances that reduce $H_2O_2$ such as catalase ($H_2O_2$ scavenger), allopurinol (xanthine oxidase XO inhibitor), acetylsalicylic acid, cyclooxygenase inhibitor (COX 1+COX 2), and VIOXX (COX2 inhibitor rofecoxib) were also investigated.

Acetylsalicylic acid and VIOXX increased FL activity marginally.

Treatment of cells with β-mercaptoethanol may also be of some use.

Figure 1B:
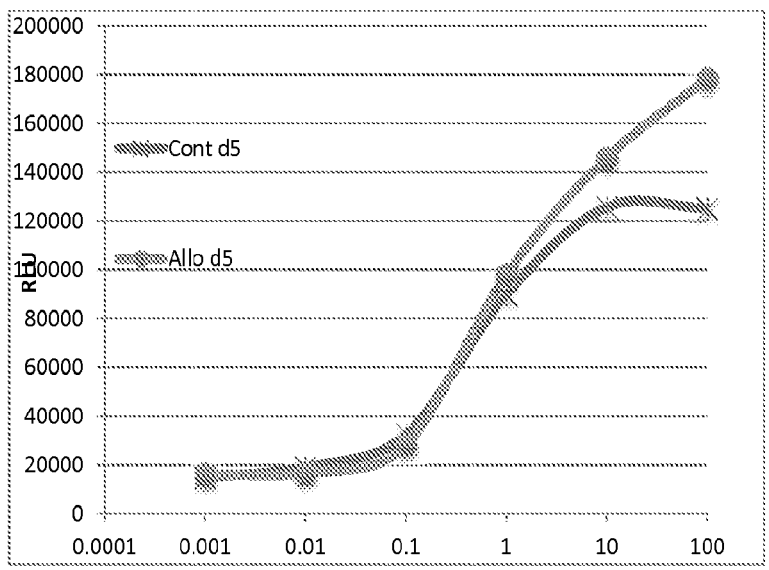
Figure 2:
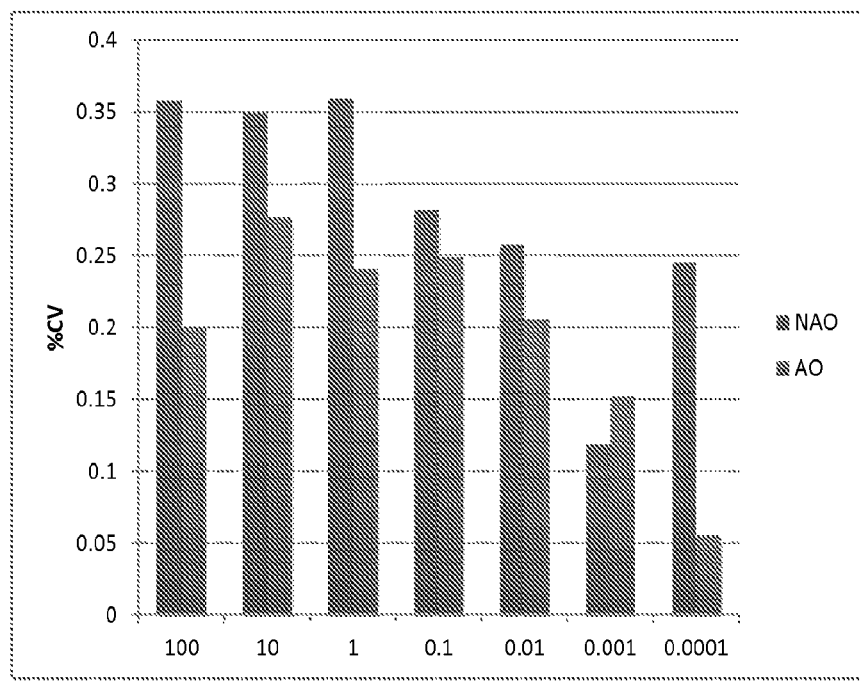
FIG. 2 is a graph showing that allopurinol (designated AO—right bar of each pair of bars; 100 mM) reduced the inter-vial coefficient of variation (% CV) compared to the control containing no allopurinol (designated NAO—left bar of each pair of bars). The X-axis is TNFα, ng/ml.
Figure 3A:
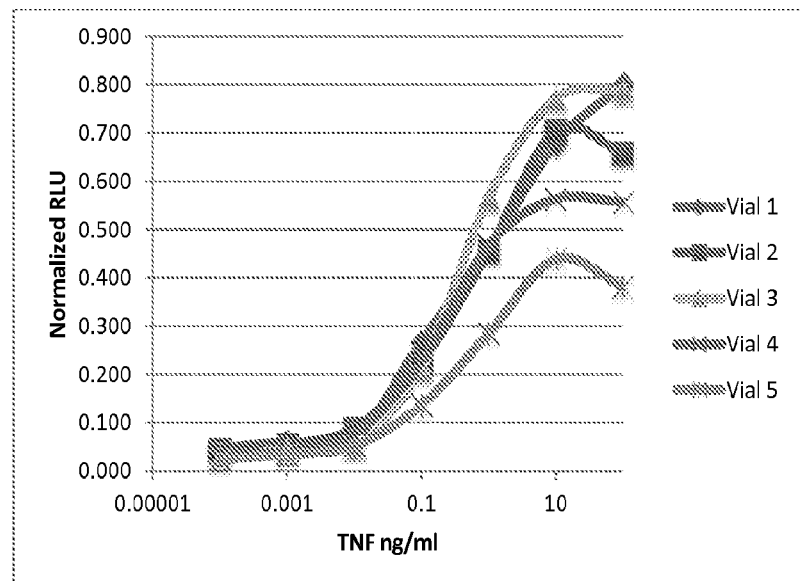
FIGS. 3A and 3B are graphs showing vial to vial variation in normalized RLU (FIG. 3A) and normalized fold induction (FIG. 3B) for the vinblastin treated cells frozen in the absence of allopurinol and the assay used in FIGS. 1A and 1B.
Figure 3B:
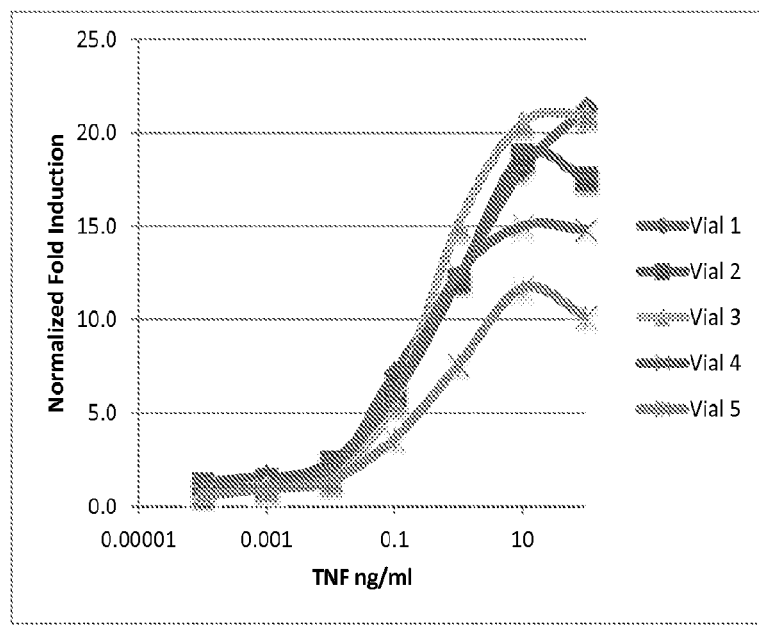
Figure 4A:
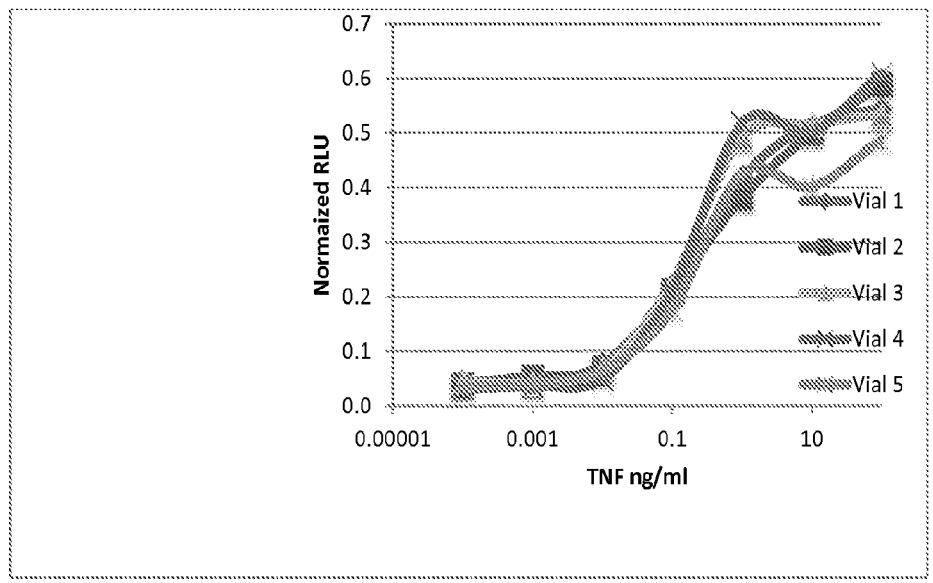
FIGS. 4A and 4B are graphs showing vial to vial variation in normalized RLU (FIG. 4A) and normalized fold induction (FIG. 4B) for vinblastin treated cells frozen in the presence of 100 μM allopurinol and the assay used in FIGS. 1A and 1B.
Figure 4B:
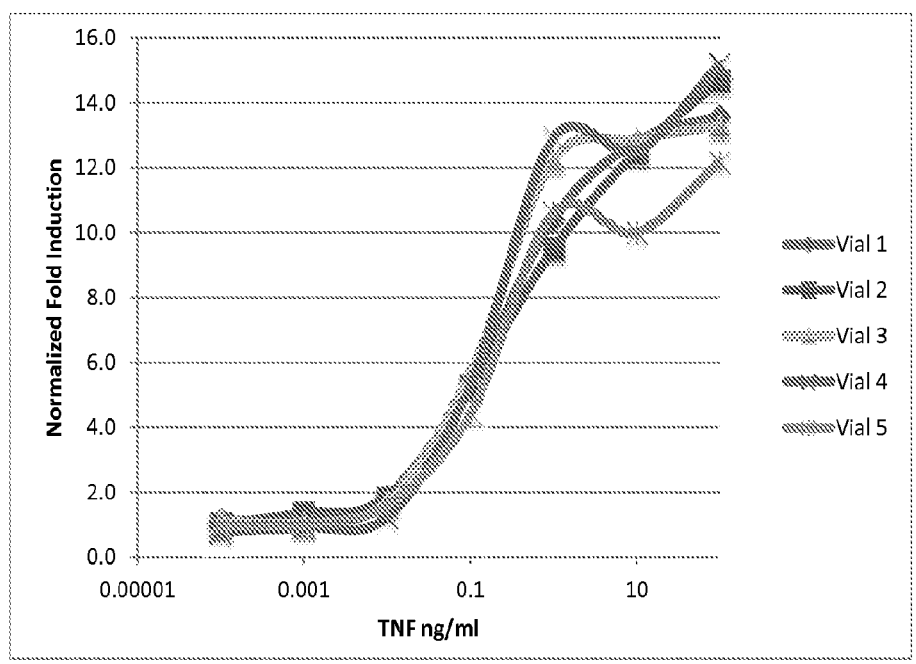

The effect of allopurinol that inhibits the enzyme xanthine oxidase which oxidizes hypoxanthine and xanthine, producing $H_2O_2$ as a byproduct, was also tested. Results show that treatment of cells with allopurinol significantly increases FL values (FIGS. 1A and 1B). Furthermore, allopurinol appeared to reduce the inter-vial coefficient of variation (FIG. 2). Allopurinol reduced intra-vial variation relative to that observed with cells treated with vinblastin alone (FIGS. 3A and 3B) whether the results were expressed as FL expression normalized with respect to constitutive RL expression (FIG. 4A: Normalized RLU values) or as normalized fold induction (FIG. 4B). Allopurinol treatment of KJL-2 cells, however, resulted in some alteration of the form of the TNFα dose response curve at concentrations of TNFα of 10 ng/ml and higher (FIGS. 4A and 4B).

Figure 5A:
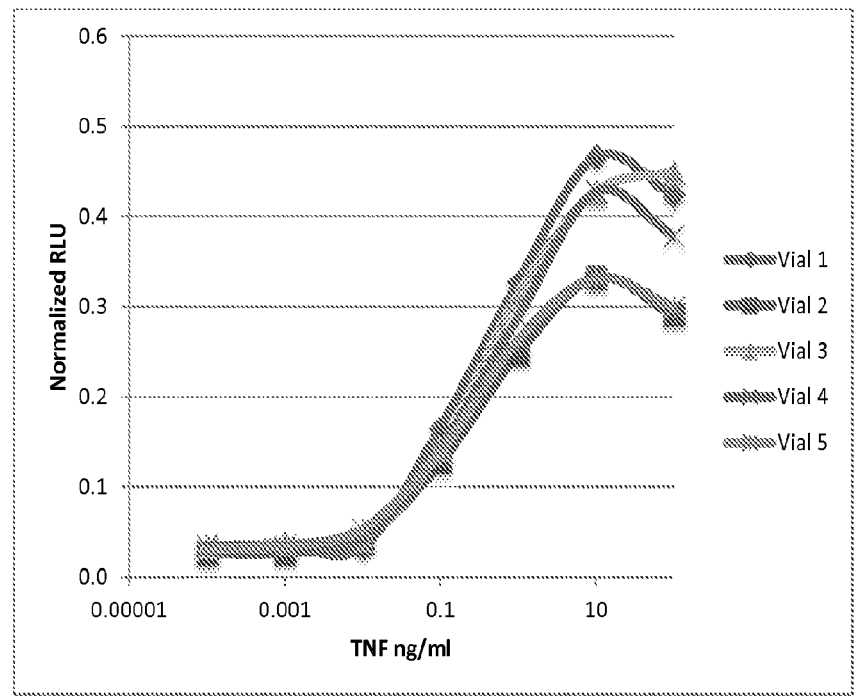
FIGS. 5A and 5B are graphs showing vial to vial variation in normalized RLU (FIG. 5A) and normalized fold induction (FIG. 5B) for vinblastin treated cells frozen in the presence of 1 mM glutathione SH (GSH) and the assay used in FIGS. 1A and 1B.
Figure 5B:
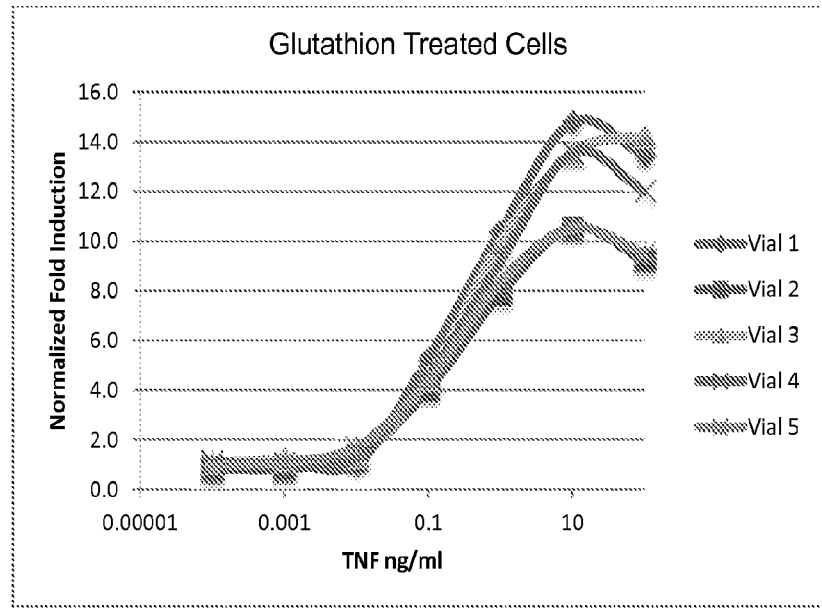
Figure 6A:
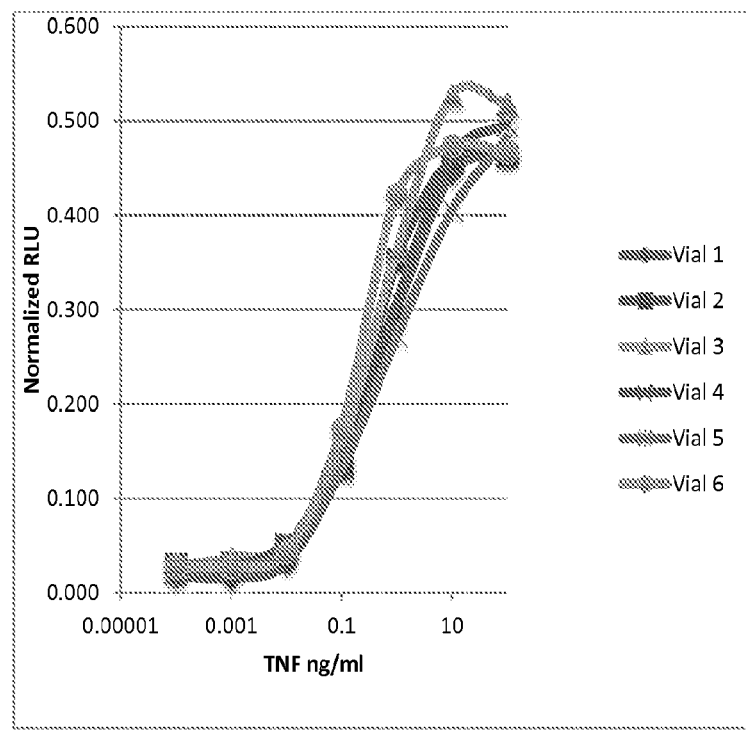
FIGS. 6A and 6B are graphs showing vial to vial variation in normalized RLU (FIG. 6A) and normalized fold induction (FIG. 6B) for vinblastin treated cells frozen in the presence of 5 mM N-acetylcystine (NAC) and the assay used in FIGS. 1A and 1B.
Figure 6B:
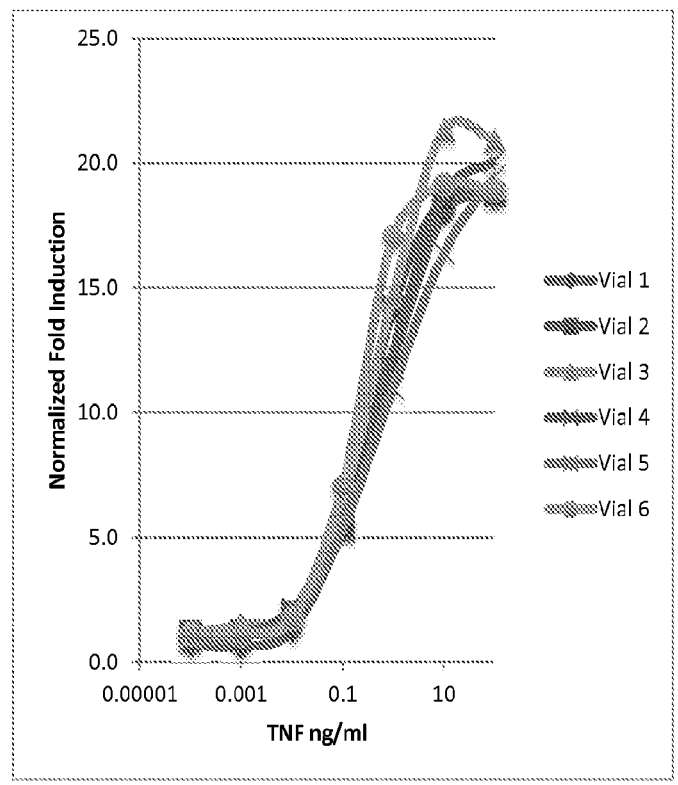

In addition to allopurinol, which inhibits the production of $H_2O_2$, the effect of glutathione SH (GSH; reduced form of glutathione) and N-acetylcystine (NAC) were also investigated in order to neutralize the $H_2O_2$ already produced within the cell. Treatment of KJL-2 cells with GSH appeared to be effective in reducing vial-to-vial variation (FIGS. 5A and 5B). N-acetylcystine appeared to be superior to GSH treatment in reducing vial-to-vial variation whether results were expressed as FL expression normalized with respect to constitutive RL expression (FIG. 6A: normalized RLU values) or as normalized fold induction (FIG. 6B).

The higher degree of variability in FL readings observed following treatment with glutathione SH relative to that observed following treatment with N-acetylcystine is most probably due to the ability of glutathione SH to interact with the NFkB pathway and therefore influence TNFα activation of FL activity. Thus, N-acetylcystine (NAC) was used as an alternative to the addition of glutathione SH in order to neutralize the $H_2O_2$ already produced within the cell without affecting the NFkB pathway.

Cells were also treated with 1 mM methionine to reduce GSH efflux from the cells both during cultivation and during the assay procedure.

Discussion

The observation that the low RLU values observed in some batches of assay-ready frozen cells do not occur immediately after freezing but take some 5 to 7 days to become apparent and that RLU values then decrease progressively with time suggests that an event(s) is occurring at −80° C. that subsequently inhibits FL activity. Since enzymatic reactions occur at markedly reduced rates at −80° C., this suggests that a chemical reaction is occurring that can result, for example, in the production and accumulation of reactive oxygen species. The results obtained with allopurinol suggest that $H_2O_2$ is the principal ROS responsible for the low FL levels seen in both certain lots of cells resulting in lot-to-lot variability and in certain individual vials resulting in vial-to-vial variability. Thus, incorporation of N-acetylcystine (NAC) both during treatment with vinblastin and in the cryopreservative medium (i.e., 40% fetal bovine serum (FBS) and 2.5% dimethylsulfoxide+10% glycerol) described in WO2004/039990; US 2004/0235157 and U.S. Pat. No. 7,470,536 was found to be an effective means of eliminating reactive oxygen species and markedly reducing both vial-to-vial and lot-to-lot variation in the performance of assay-ready frozen cells.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Law G H, Gandelman O A, Tisi L C, Lowe C R, Murray J A (2006) Mutagenesis of solvent-exposed amino acids in Photinus pyralis luciferase improves thermostability and pH-tolerance. Biochem J 397: 305-312.

Baggett B, Roy R, Momen S, Morgan S, Tisi L, et al. (2004) Thermostability of firefly luciferases affects efficiency of detection by in vivo bioluminescence. Mol Imaging 3: 324-332.

Thompson J F, Geoghegan K F, Lloyd D B, Lanzetti A J, Magyar R A, et al. (1997) Mutation of a protease-sensitive region in firefly luciferase alters light emission properties. J Biol Chem 272: 18766-18771.

Loening A M, Fenn T D, Wu A M, Gambhir S S (2006) Consensus guided mutagenesis of Renilla luciferase yields enhanced stability and light output. Protein Eng Des Sel 19: 391-400.

Nakajima S, Kato H, Takahashi S, Johno H, Kitamura M. Inhibition of NF-κB by MG132 through ER stress-mediated induction of LAP and LIP. FEBS Lett. 2011 Jul. 21; 585(14):2249-54. Epub 2011 May 27.

Jüllig M, Zhang W V, Ferreira A, Stott N S. MG132 induced apoptosis is associated with p53-independent induction of pro-apoptotic Noxa and transcriptional activity of beta-catenin. Apoptosis. 2006 11(4):627-41.

What is claimed is:

1. An assay-ready eukaryotic cell stored frozen in a composition comprising a cryopreservative and allopurinol at a concentration in the composition in a range of about 50 to 200 μM.

2. The assay-ready frozen eukaryotic cell of claim 1, wherein the concentration of allopurinol in the composition is in a range of about 75 to 150 μM.

3. The assay-ready frozen eukaryotic cell of claim 1, wherein the concentration of allopurinol in the composition is about 100 μM.

4. The assay-ready frozen eukaryotic cell of claim 1, wherein said cryopreservative is dimethylsulfoxide (DMSO).

5. The assay-ready frozen eukaryotic cell of claim 4, wherein the amount of DMSO in the composition is about 10%.

6. The assay-ready frozen eukaryotic cell of claim 1, wherein said cryopreservative is glycerol.

7. The assay-ready frozen eukaryotic cell of claim 1, wherein said cryopreservative is a combination of about 2.5% dimethylsulfoxide (DMSO) and about 10% glycerol.

8. The assay-ready frozen eukaryotic cell of claim 1, wherein the composition further comprises fetal bovine serum (FBS).

9. The assay-ready frozen eukaryotic cell of claim 8, wherein the amount of FBS in the composition is about 40%.

10. The assay-ready frozen eukaryotic cell of claim 1, wherein the composition further comprises a scavenger of reactive oxygen species.

11. The assay-ready frozen eukaryotic cell of claim 10, wherein said scavenger of reactive oxygen species is N-acetylcysteine (NAC) or glutathione SH (GSH).

12. The assay-ready frozen eukaryotic cell of claim 11, wherein the concentration of NAC is in a range of about 1 mM to 10 mM.

13. The assay-ready frozen eukaryotic cell of claim 11, wherein the concentration of NAC is about 5 mM.

14. The assay-ready frozen eukaryotic cell of claim 11, wherein the concentration of GSH is about 1 mM.

15. The assay-ready frozen eukaryotic cell of claim 1, wherein allopurinol is at a concentration of about 100 µM and said composition further comprises about 40% FBS and a concentration of NAC in a range of about 2.5 mM to 5 mM.

16. The assay-ready frozen eukaryotic cell of claim 1, containing a reporter gene construct comprising a nucleotide sequence encoding a reporter gene product operatively linked to one or more transcriptional control elements that is regulated by the signal transduction activity of a cell surface protein in response to an extracellular signal.

17. The assay-ready frozen eukaryotic cell of claim 1, in which the cells were treated with an anti-mitotic or pro-apoptotic agent prior to being frozen for storage.

18. The assay-ready frozen eukaryotic cell of claim 1, wherein the eukaryotic cell is selected from the group consisting of a mammalian, avian, fish, insect, and yeast cell.

19. The assay-ready frozen eukaryotic cell of claim 1, wherein the eukaryotic cell is a human cell.

20. The assay-ready frozen eukaryotic cell of claim 18, wherein the eukaryotic cell is a chicken cell.

21. The assay-ready frozen eukaryotic cell of claim 18, wherein the eukaryotic cell is a zebrafish cell.

22. The assay-ready frozen eukaryotic cell of claim 19, wherein the human cell is a promonocytic cell.

23. A kit for conducting an assay, comprising:
   a testing device having a plurality of wells; and
   a reagent comprising a plurality of the assay-ready frozen cell of claim 1.

24. The kit of claim 23, wherein said testing device is a microtiter plate.

25. The kit of claim 23, wherein said reagent is disposed in the wells of said testing device.

26. A method for preparing the assay-ready frozen eukaryotic cell of claim 1, comprising:
   adding a composition comprising a cryopreservative and an inhibitor of xanthine oxidase to a eukaryotic cell; and
   cooling the cell at a rate of about 1° C. per minute until about −80° C. for frozen storage of the assay-ready eukaryotic cell, thereby improving the performance, upon thawing, of the assay-ready cell in an assay.

27. The method of claim 26, wherein, prior to adding the composition comprising a cryopreservative and an inhibitor of xanthine oxidase to the eukaryotic cell, the eukaryotic cell is treated with an anti-mitotic or pro-apoptotic agent and then the eukaryotic cell is removed from contact with the anti-mitotic or pro-apoptotic agent.

28. The method of claim 27, wherein the anti-mitotic or pro-apoptotic agent is vinblastin.

29. The method of claim 26, wherein a plurality of assay-ready frozen eukaryotic cells are prepared and stored frozen in a plurality of separate individual vials or containers and the method minimizes the variability between individual vials or containers in the performance of the assay-ready frozen eukaryotic cells, upon thawing, in an assay.

* * * * *